US011617800B2

(12) United States Patent
Delehanty et al.

(10) Patent No.: US 11,617,800 B2
(45) Date of Patent: Apr. 4, 2023

(54) NANOPARTICLE-ENHANCED ACTIVITY OF A POTASSIUM CHANNEL-BLOCKING PEPTIDE

(71) Applicant: The Government of the United States of America, as represented by the Secretary of the Navy, Arlington, VA (US)

(72) Inventors: James B. Delehanty, Washington, DC (US); Megan Muroski, Alexandria, VA (US); Eunkeu Oh, Alexandria, VA (US); Jeffrey R. Deschamps, Laurel, MD (US)

(73) Assignee: The Government of the United States of America, as represented by the Secretary of the Navy, Washington, DC (US)

( * ) Notice: Subject to any disclaimer, the term of this patent is extended or adjusted under 35 U.S.C. 154(b) by 281 days.

(21) Appl. No.: 17/016,905

(22) Filed: Sep. 10, 2020

(65) Prior Publication Data

US 2021/0077633 A1 Mar. 18, 2021

Related U.S. Application Data

(60) Provisional application No. 62/899,186, filed on Sep. 12, 2019.

(51) Int. Cl.
*A61K 47/69* (2017.01)
*A61K 38/17* (2006.01)
*A61K 47/52* (2017.01)

(52) U.S. Cl.
CPC .......... *A61K 47/6929* (2017.08); *A61K 38/17* (2013.01); *A61K 47/52* (2017.08)

(58) Field of Classification Search
CPC ..... A61K 47/6929; A61K 47/52; A61K 38/17
See application file for complete search history.

(56) References Cited

U.S. PATENT DOCUMENTS

| 6,979,572 B1 | 12/2005 | Lu |
| 2012/0310140 A1* | 12/2012 | Kramer ............... A61K 9/0085 |
| | | 604/93.01 |
| 2018/0303937 A1 | 10/2018 | Da Silva et al. |
| 2019/0225658 A1 | 7/2019 | Noujaim et al. |

OTHER PUBLICATIONS

Chiara Paviolo and Paul R. Stoddart. "Gold nanoparticles for modulating neuronal behavior," Nanomaterials, 2017, 7, 1-14. (Year: 2010).*
J.B. Delehanty, et al. "Peptides for the specific intracellular delivery and targeting of nanoparticles: implications for developing nanoparticle-mediated drug delivery," Therapeutic delivery, vol. 1, issue 3, Sep. 2010, 411-433. (Year: 2010).*
International Search Report dated Jan. 6, 2021 in PCT/US2020/050287.
Muroski et al., "Display of Potassium Channel-Blocking Tertiapin-Q Peptides on Gold Nanoparticles Enhances Depolarization of Cellular Membrane Potential," Jan. 2019, Particle and Particle Systems Characterization 36(3):1800493 DOI: 10.1002/ppsc.201800493.
Jin et al., "Synthesis of a Stable Form of Tertiapin: A High-Affinity Inhibitor for Inward-Rectifier K+ Channels" Biochemistry 1999, 38, 14286-14293.

* cited by examiner

*Primary Examiner* — Michael P Cohen
(74) *Attorney, Agent, or Firm* — US Naval Research Laboratory; Roy Roberts

(57) ABSTRACT

A nanoparticle (NP)-peptide conjugate provides efficient steric hindrance/blockage of cellular membrane potassium ($K^+$) channels to mediate depolarization of cellular membrane potential.

1 Claim, 5 Drawing Sheets

Specification includes a Sequence Listing.

Tertiapin-Q (TPN-Q)
[acetyl]-ALCNCNRIIIPHQCWKKCGKK
Modified
[alkyne]-LAGWGPALCNCNRIIIPHQCWKKCGKK
FIG. 1A
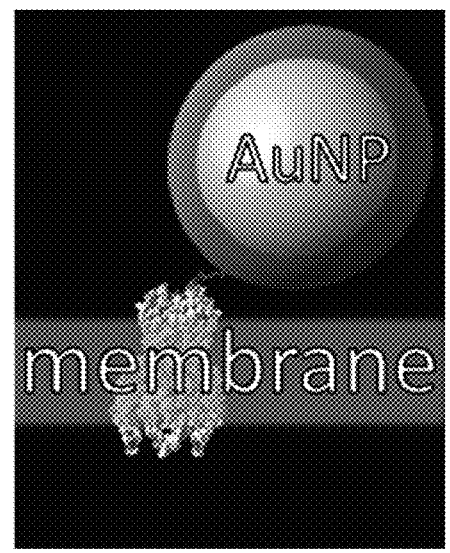
FIG. 1B
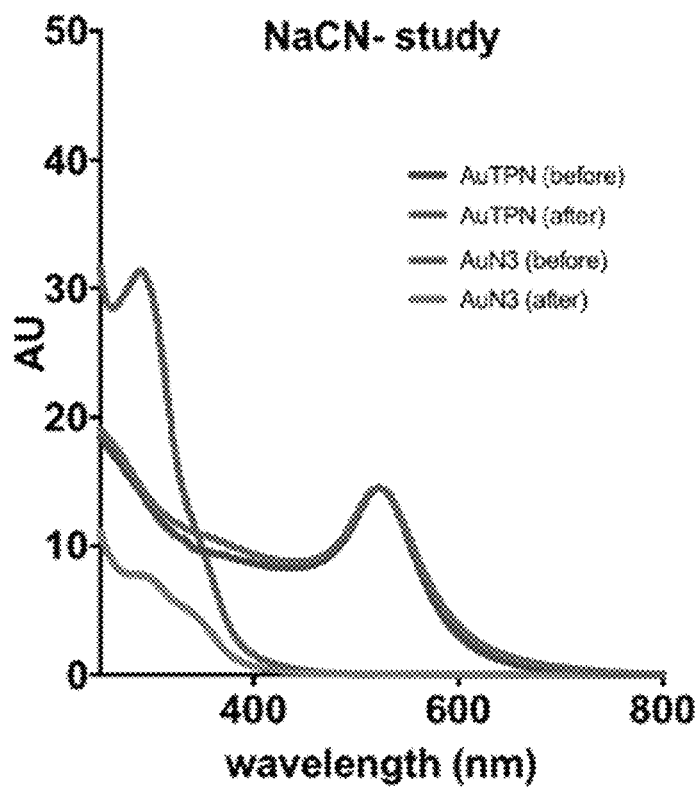
FIG. 1C
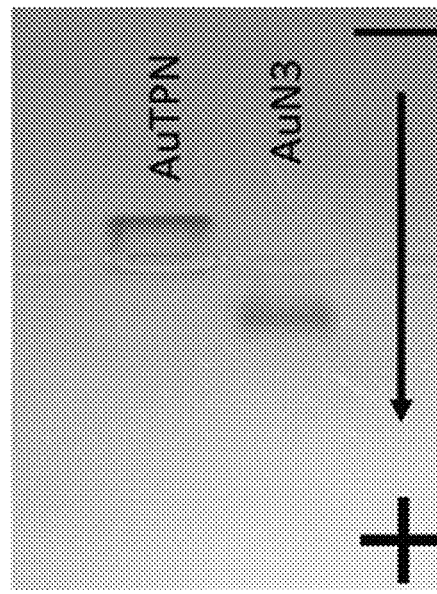
FIG. 1D

NANOPARTICLE-ENHANCED ACTIVITY OF A POTASSIUM CHANNEL-BLOCKING PEPTIDE

CROSS-REFERENCE TO RELATED APPLICATIONS

This applications claims the benefit of U.S. Provisional Patent Application No. 62/899,186 filed Sep. 12, 2019, the entirety of which is incorporated herein by reference.

FEDERALLY-SPONSORED RESEARCH AND DEVELOPMENT

The United States Government has ownership rights in this invention. Licensing inquiries may be directed to Office of Technology Transfer, US Naval Research Laboratory, Code 1004, Washington, D.C. 20375, USA; +1.202.767.7230; techtran@nrl.navy.mil, referencing NC 109,399.

STATEMENT REGARDING PRIOR DISCLOSURES BY THE INVENTOR(S)

A prior disclosure, Muroski, M. E., Oh, E., Deschamps, J. R., Delehanty, J. B., *Part. Part. Syst. Charact.* 2019, 36, 1800493, was made by the inventors.

BACKGROUND

The therapeutic modulation of membrane potential of electrically excitable cells has gained interest in recent years as membrane potential regulates proliferation, migration and communication among neuronal cells and contraction in muscle cells. Furthermore, while normal cells exhibit resting membrane potentials between −60 to −100 mV, cancer cells tend to have elevated resting membrane potentials between −55 mV to +5 mV. Exploiting the large differences in membrane potential provides a unique opportunity for researchers to target therapeutics specifically to cancer cells.

One way to modulate cell membrane potential is by blocking potassium ($K^+$) channels. Existing drugs that block $K^+$ channels include dalfampridine, dofetilide, and amiodarone. The experimental drug tetraethylammonium also blocks potassium channels. These drugs tend to be nonspecific, with a range of binding affinities and off-target effects, and their binding is often irreversible A need exists for new potassium channel blockers.

BRIEF SUMMARY

A nanoparticle (NP)-peptide conjugate provides efficient steric hindrance/blockage of cellular membrane potassium ($K^+$) channels to mediate depolarization of cellular membrane potential.

BRIEF DESCRIPTION OF THE DRAWINGS

FIGS. 1A through 1D present a computational model for the AuNP-TPN-Q bioconjugate and characterization of the conjugated assembly. FIG. 1A provides the amino acid sequences of TPN-Q (top) and spacer-modified (in red, bottom) TPN-Q peptides. FIG. 1B illustrates a computational model of the AuNP-TPN-Q complex bound to a Kir channel: the AuNP core (yellow) is 10 nm; membrane (blue) is 5 nm thick. FIG. 1C shows the absorbance of the AuNP-TPN-Q conjugates and AuNP-$N_3$ before and after treatment with NaCN. FIG. 1D is an agarose gel characterization showing the inhibited migration of the AuNPs after conjugation to the TPN-Q peptide.

FIG. 2A presents results of real time monitoring of TPN-Q-induced depolarization in undifferentiated (−NGF) and differentiated (+NGF) PC12 cells. FIG. 2B compares the baseline and final time points. FIG. 2C provides stacked confocal images (each image combines four z-planes) of initial and final time points of TPN-Q incubation with undifferentiated (−NGF) and differentiated (+NGF) PC-12 cells. Images were acquired at 60 fold magnification.

FIGS. 3A-3C depict the labeling of PC-12 cells with AuNP-TPN-Q/FITC conjugates. FIG. 3A shows nuclear (NucBlue), AuNP-TPN-Q/FITC, Rhod-PE staining and overlay images of PC-12 cells (+NGF) labeled with AuNP-TPN-Q/FITC (100 nM) imaged after 20 min incubation. FIG. 3B shows individual stack slices with a 0.15 μm step size increment on PC-12 cells (+NGF) labeled with AuNP-TPN-Q/FITC. FIG. 3C is a rendered 3D image of plasma membrane association of AuNP-TPN-Q/FITC (green) and Rhod-PE (red). The cell nucleus is in blue.

FIG. 4 shows the normalized change in depolarization with equivalent concentration of TPN-Q peptide as either free peptide or as AuNP-TPN-Q. Depolarization was quantified by measuring DiBAC4(3) fluorescence response as a function of time.

FIG. 5 shows the reversibility of the depolarization.

DETAILED DESCRIPTION

Definitions

Before describing the present invention in detail, it is to be understood that the terminology used in the specification is for the purpose of describing particular embodiments, and is not necessarily intended to be limiting. Although many methods, structures and materials similar, modified, or equivalent to those described herein can be used in the practice of the present invention without undue experimentation, the preferred methods, structures and materials are described herein. In describing and claiming the present invention, the following terminology will be used in accordance with the definitions set out below.

As used herein, the singular forms "a", "an," and "the" do not preclude plural referents, unless the content clearly dictates otherwise.

As used herein, the term "and/or" includes any and all combinations of one or more of the associated listed items.

As used herein, the term "about" when used in conjunction with a stated numerical value or range denotes somewhat more or somewhat less than the stated value or range, to within a range of ±10% of that stated.

Overview

Described herein is a nanoparticle (NP)-peptide conjugate that provides efficient steric hindrance/blockage of cellular membrane potassium ($K^+$) channels to mediate depolarization of cellular membrane potential.

Inwardly-rectifying $K^+$ (Kir) channels have a water-filled pore through which they preferentially pass current (positive charge) more easily in the inward direction (into the cell) than in the outward direction. These channels play a critical role in stabilizing the resting membrane potential of the cell. A number of ions (e.g., $Mg^{2+}$), polyamines, and drugs have been shown to block Kir channels, resulting in depolarization of membrane potential. Additionally, peptides derived from various species have been shown to bind to the outer vestibule of the $K^+$ channel pore to block the movement of $K^+$ ions. Specifically, tertiapin (TPN), a 21-mer peptide derived from honey bee venom, has been shown to interact with one to one stoichiometry to specifically block Kir channels, ROMK1 homoultimers (Kir1.1), the G-proteincoupled inwardly rectifying potassium channel 1/4 (Kir 3.1/3.4), as well as native BK-type K$^+$ channels. TPN binds with nanomolar affinity (~2 nM for ROMK1 channels) to the channel through its alpha helix.

Figure 2A:
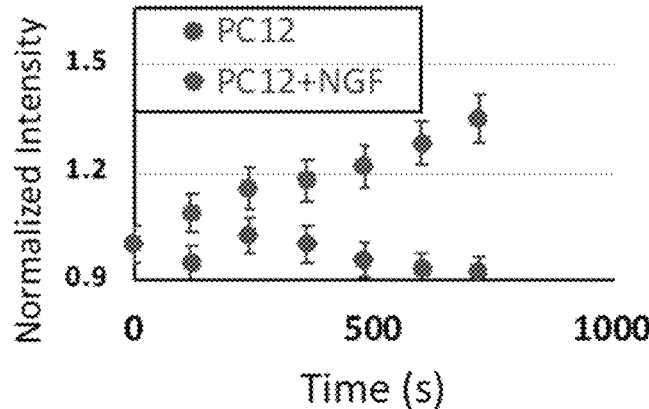

The native TPN peptide is unstable due to an oxidizable methionine (M) residue at position 13. This residue can be replaced with a glutamine (Q) to obtain a stable derivative denoted as TPN-Q with the sequence ALCNCN-RIIIPHQCWKKCGKK (SEQ ID NO: 1). When the inventors conjugated TPN-Q to gold nanoparticles (AuNP), the resulting AuNP-TPN-Q bioconjugate exhibited enhanced membrane depolarization activity compared to the free TPN-Q peptide.

The AuNP is synthesized as an azide-terminated particle which is bound to TPN-Q through click chemistry bioconjugation, although other linkage chemistries could also be implemented. The peptide is appended to the AuNP surface through the addition of a six amino acid spacer/linker located on the N-terminal portion of TPN-Q to provide spacing between the AuNP and the membrane channel binding site of the peptide. It is expected that the linker serves to decrease steric hindrance that could otherwise abrogate the interaction of the peptide with the membrane channel. Spacers other than that used in the examples are expected to be similarly functional, for example those of different sequences and lengths.

Membrane potential depolarization of neuron-like PC-12 cells was examined with and without the presence of the AuNP-TPN-Q complex and the free TPN-Q peptide. The AuNP-TPN-Q conjugate significantly augments the depolarization of membrane potential in differentiated PC-12 cells compared to the free peptide alone. Specifically, the channel blocking activity of the AuNP-TPN-Q complex was observed to be 2- to 3-fold more efficient than the free TPN-Q peptide. Further, in a concentration-dependent manner, the complex displays faster depolarization kinetics compared to the free TPN-Q peptide.

Examples

The sequences of the TPN-Q peptide and its modified derivative used for conjugation are shown in FIG. 1A. The native TPN peptide is unstable due to the oxidizable methionine (M) residue at position 13. This residue is often replaced with a glutamine (Q) to obtain a stable derivative denoted as TPN-Q.TPN-Q interacts with the inward-rectifier K$^+$ (Kir) channel via its C-terminal alpha helix (amino acid resides His 12-Gly 19).

For production of the AuNP-TPN-Q bioconjugate, the TPN-Q peptide was modified at its N-terminus with a 6 amino acid sequence LAGWGP (SEQ ID NO: 2) designed to act as a spacer between the peptide and the surface of the gold nanoparticle, so that the spacer-modified TPN-Q had an overall sequence of LAGWGPALCNCN-RIIIPHQCWKKCGKK (SEQ ID NO: 3). An alkyne functional group on the N-terminal leucine residue mediates click chemistry conjugation to the azide-functionalized AuNP surface. The AuNP was functionalized to have~20% functional azide groups on the surface to mediate covalent conjugation to the modified alkyne group at the N-terminus of TPN-Q. The AuNP-TPN-Q conjugate is believed to be the first bioconjugate system to combine a nanoparticle and a potassium channel blocking peptide to provide augmented function that is not afforded by the free peptide alone.

On a peptide concentration basis, the AuNP-TPN-Q conjugate was found to mediate an average 2- to 3-fold greater depolarization response compared to the free TPN-Q peptide. Furthermore, in a concentration-dependent manner, the AuNP-TPN-Q conjugate exhibits an enhanced rate of cellular depolarization.

FIG. 1B shows a computational model of the ensemble conjugate and its proposed interaction of the AuNP-TPN-Q conjugate with a membrane-resident K$^+$ channel. The AuNP core (10 nm diameter) in the image is denoted in yellow and includes the capping ligand mixture which is comprised of 80% PEG$_{550}$-OMe and 20% PEG$_{600}$-azide (shown as a grey encapsulation around the AuNP). For representative purposes, one TPN-Q peptide is shown bound to the surface of the AuNP. The schematic is drawn to scale demonstrating the α-helical peptide bound to the K$^+$ channel (ball and stick diagram). The blue line represents the plasma membrane bilayer of living cells (~5 nm thick).

Analysis of the computational model predicted that the linker would provide enough clearance for the TPN-Q to interact with the K$^+$ channel while simultaneously allowing the AuNP to sit closely to the cell surface. It was desired to verify the assembly of the peptide-AuNP system. FIG. 1C shows the absorption spectra of AuNP-TPN-Q conjugates before (blue) and after (red) digestion of the AuNP with sodium cyanide to dissolve the AuNP and compared to the unfunctionalized AuNP-N$_3$ before (purple) and after (green). Quantification of the amount of peptide that was bound to the surface of the AuNP (and subsequently released by the AuNP digestion) was determined through tryptophan absorbance at 280 nm. This indicated that ~100 peptides were conjugated to the AuNP surface. Gel electrophoresis analysis showed that after conjugation to the TPN-Q peptide (which imparts a net positive charge to the AuNP) the AuNPs preferentially migrated towards the anode (negative post) (FIG. 1D). Cumulatively, these data show the stable, quantitative conjugation of the TPN-Q peptide to the AuNP surface The function of the TPN-Q peptide was examined in neuron-like cells, namely the PC-12 cell line which is derived from a pheochromocytoma of the rat adrenal medulla. These cells can be induced to adopt a neuron-like phenotype (morphologically and functionally) when cultured in the presence of nerve growth factor (NGF), making them suited for monitoring the regulation and function of ion channels. Undifferentiated (−NGF) and differentiated (+NGF) PC-12 cells were exposed to TPN-Q with the change in depolarization monitored in real time. Membrane depolarization was monitored using the potentiometric indicator DiBAC4(3) (bis-(1,3-dibutylbardituric acid) trimethine oxonol) before and after incubation of the cells with TPN-Q peptide. DiBAC4(3) is a membrane potential-tracking probe that inserts into the plasma cellular membrane and exhibits an increase in fluorescence upon cellular depolarization.

Figure 2B:
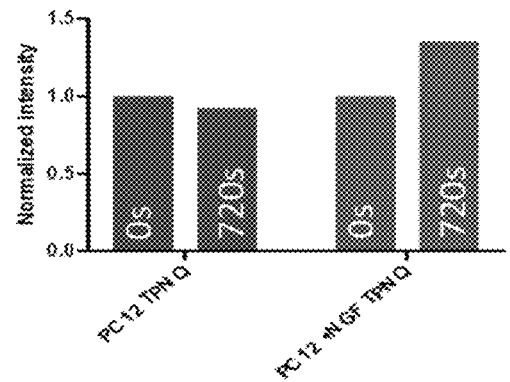
Figure 2C:
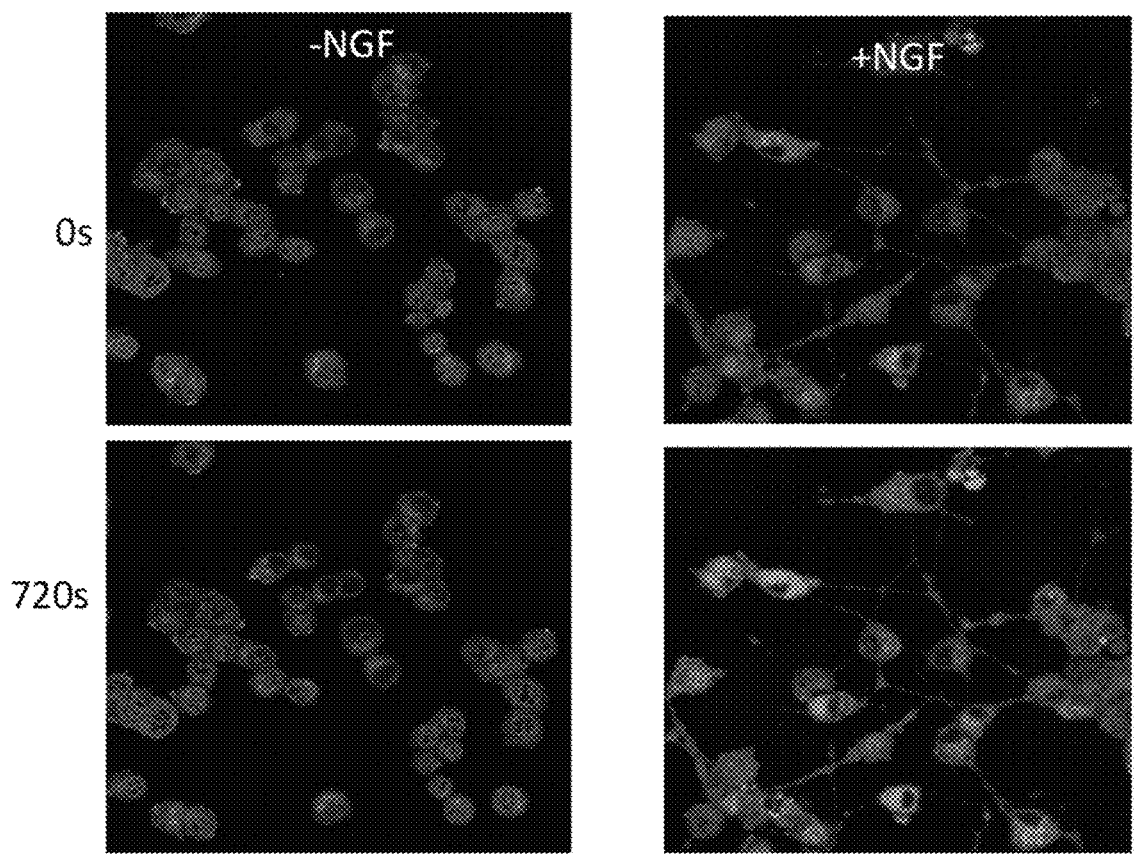
Figure 3A:
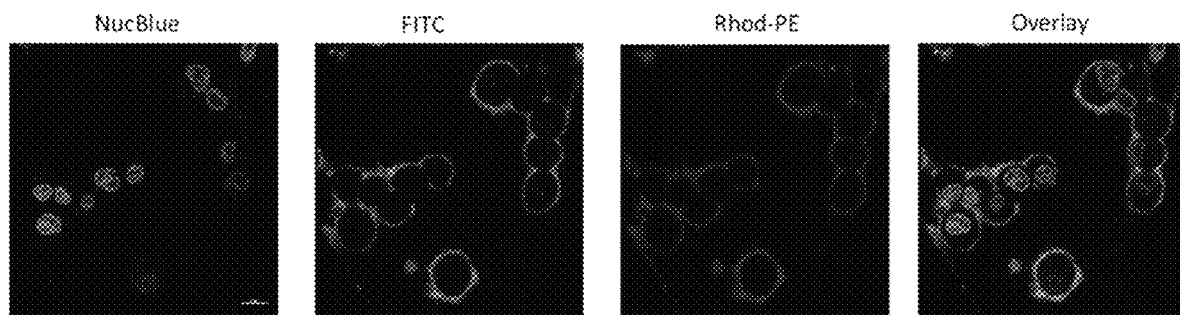
Figure 3B:
Figure 3C:
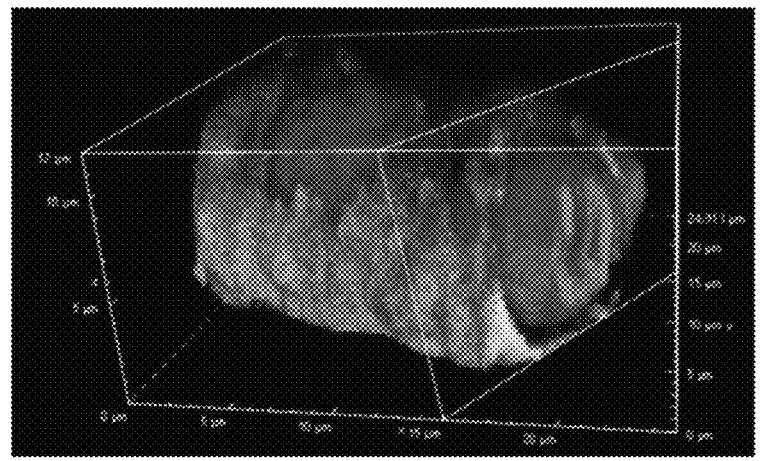
Figure 4:
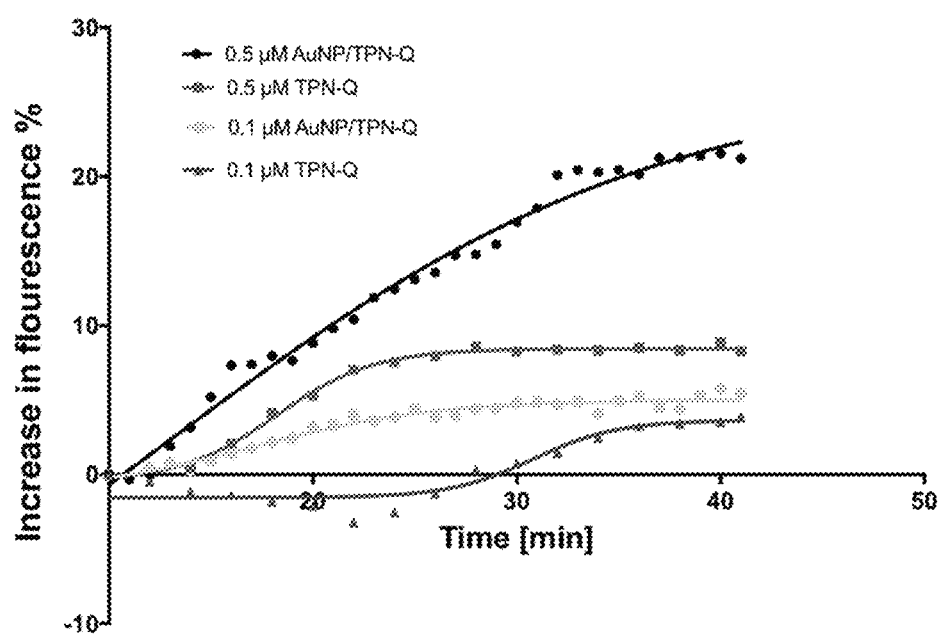

The data in FIGS. 2A-2C show that while undifferentiated PC-12 cells showed negligible depolarization (as evidenced by minimal change in DiBAC4(3) fluorescence intensity) in the presence of 500 nM TPN-Q, PC-12 cells differentiated with NGF showed a~30% increase in fluorescence. FIG. 2A is a plot of the change in fluorescence intensity of the DiBAC4(3) probe every 120 s. After initial loading with DiBAC4(3), the cells were imaged to acquire a baseline of the DiBAC4(3) emission and then imaged over time after adding TPN-Q. The fluorescence intensities at the initial and final time point are graphically represented in FIG. 2B, and can be observed in the stack focused confocal images (FIG. 2C). These results demonstrate the successful differentiation of PC-12 cells with NGF that renders them more responsive to the depolarization effects of K$^+$ channel blocking TPN-Q peptide The membrane labeling efficiency of the ensemble AuNP-TPN-Q conjugate system on PC-12 cells was examined. Since TPN-Q binds to the channel directly on the plasma membrane of the cell, it was expected that the conjugate complex would surround the cell with minimal signs of internalization. For visualization, AuNP-TPN-Q conjugates were functionalized with fluorescein in the form of fluorescein isothiocyanate (FITC). Upon incubation of PC-12 (+NGF) cells with 100 nM AuNP-TPN-Q/FITC complex followed by extensive washing, we observed distinct plasma membrane labeling. This was confirmed by co-staining with the membrane marker, Rhod-PE (FIG. 3A). Analysis of individual z-stack slices at 0.15 μm step size (FIG. 3B) and rendered 3D stack (FIG. 3C) confirmed the association of the AuNP-TPN-Q/FITC conjugate with the plasma membrane To determine the ability of AuNP-TPN-Q to mediate the depolarization of cellular membrane potential, the time-resolved increase in DiBAC4(3) in PC-12 cells differentiated with NGF was measured. After obtaining baseline fluorescence of the dye-labeled cells, PC-12 (+NGF) cells were incubated with AuNP-TPN-Q or free TPN-Q and the fluorescence response was monitored over time. This was done to specifically compare the depolarization efficiency of the AuNP-TPN-Q conjugate to the free TPN-Q peptide. Cells were incubated with equivalent amounts of TPN-Q peptide (presented as either a AuNP conjugate or as free peptide in solution) (FIG. 4). At a TPN-Q concentration of 0.5 μM, the AuNP form of the peptide facilitated a maximal depolarization response that was 3-fold greater than that of the free peptide. When the TPN-Q peptide concentration was reduced to 0.1 μM, the AuNP-TPN-Q conjugate mediated a~2-fold greater depolarization response than the free peptide. We also observed differences between AuNP-TPN-Q and free TPN-Q in the rate of membrane depolarization that were dependent on the TPN-Q peptide concentration. At 0.5 μM, the half-maximal depolarization response ($t_{1/2}$) was attained at ~17 min for both the AuNP-TPN-Q conjugate and the free TPN-Q peptide. When the peptide concentration was reduced to 0.1 μM, however, the $t_{1/2}$ for maximal depolarization was reached at ~22 min for the AuNP-TPN-Q conjugate while the $t_{1/2}$ for the free TPN-Q peptide was ~31 min.

The observed augmented depolarization effect mediated by the AuNP form of the TPN-Q peptide (relative to the free peptide) can potentially be attributed to a number factors including (1) the enhanced stability of the TPN-Q peptide when displayed on the surface of the AuNP, (2) the augmented local peptide concentration when the TPN-Q peptide is displayed at high copy number on the AuNP surface that facilitates more rapid and stable interaction of the TPN-Q peptide with the membrane $K^+$ channel, and/or (3) the enhanced settling time of the AuNP-TPN-Q conjugate in solution compared to the free peptide which promotes faster interaction of the peptide with the membrane channel. The increase in TPN-Q peptide efficacy shown here has the potential to dramatically improve the $K^+$ channel-targeted drug therapies and enable new materials for the wireless control of cellular behavior/function.

Figure 5:
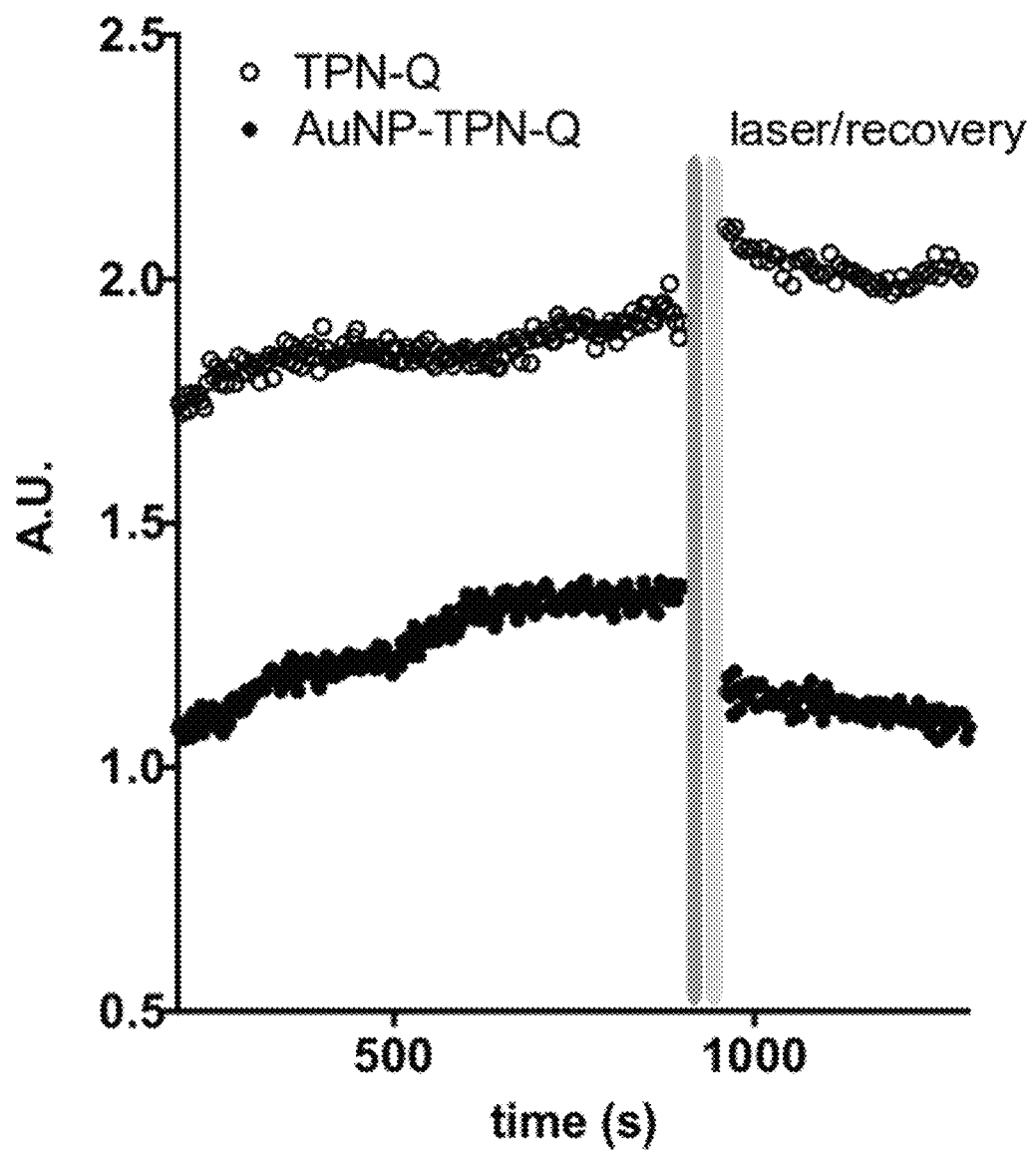

As seen in FIG. 5, PC12 cells depolarized with 100 nM AuNP-TPN-Q (closed circle) show the ability to undergo reversibility of depolarization by heating the AuNP using a 561 nm laser pulse (5 mW, 30 sec) (green vertical line) followed by a wash step and 30 sec recovery time. Soluble TPN-Q peptide (control, open circle) does not show this effect, demonstrating the role of the AuNP in mediating the thermal-assisted dissociation of the AuNP-TPN-Q conjugate from the K channel Further Embodiments This technique might be extended to a wide range of AuNP sizes, for example those in the range of 2 nm to 200 nm. Nanoparticles of other compositions are contemplated.

The click chemistry is amenable to the attachment of the TPN-Q peptide to other NP species (e.g., liposomes, micelles, semiconductor nanocrystals/quantum dots, magnetic nanoparticles).

Other forms of attachment chemistry might be used.

Other drugs can be attached (by cleavable, triggerable linkers) to the AuNP-TPN-Q conjugate for multifunctionality.

Because activity is reversible by using light to heat the AuNP (and thus perturb TPN-Q/channel interaction), it is expected that heat achieved by ultrasound or radiofrequency could achieve the same result.

Contemplated herein are medicaments and therapies including nanoparticle/peptide conjugates as described herein. Potential uses of the construct include NP-based therapeutics for the activation of neurons and muscle cells for non-invasive brain and muscle cell stimulation through the controlled modulation of membrane potential.

Advantages

By appending the TPN-Q peptide to a gold nanoparticle carrier (thereby controlling its copy number and orientation of display) the biological activity of the TPN-Q peptide (i.e., K+ channel-blocking activity) is enhanced/augmented.

When labeled with a dye, the AuNP-TPN-Q can be easily tracked and its binding to the plasma membrane can be visualized.

Concluding Remarks

All documents mentioned herein are hereby incorporated by reference for the purpose of disclosing and describing the particular materials and methodologies for which the document was cited.

Although the present invention has been described in connection with preferred embodiments thereof, it will be appreciated by those skilled in the art that additions, deletions, modifications, and substitutions not specifically described may be made without departing from the spirit and scope of the invention. Terminology used herein should not be construed as being "means-plus-function" language unless the term "means" is expressly used in association therewith.

REFERENCES

Identification and Stable Modification of Tertiapin
Jin W, Lu Z. A Novel High-Affinity Inhibitor for Inward-Rectifier K+ Channels *Biochemistry* 1998. 37 (38), 13291-13299 DOI: 10.1021/bi981178p
Jin W and Lu Z. Synthesis of a Stable Form of Tertiapin: A High-Affinity Inhibitor for Inward-Rectifier $K^+$ Channels, *Biochemistry* 1999. 38 (43), 14286-14293, DOI: 10.1021/bi991205r
Ramu Y, Xu Y, Lu Z. Engineered specific and high-affinity inhibitor for a subtype of inward-rectifier $K^+$ channels. *Proceedings of the National Academy of Sciences of the United States of America.* 2008; 105(31):10774-10778. DOI:10.1073/pnas.0802850105.
Analysis of Depolarization Via Nanoparticle and Cell Membrane Interactions
Warren E A K, Payne C K. Cellular binding of nanoparticles disrupts the membrane potential. *Royal Society of Chemistry Advances,* 2015 5, 13660-13666.
Chowdhury S M, Xie S, Fang J, Lee S K, Sitharaman B. Nanoparticle-Facilitated Membrane Depolarization-Induced Receptor Activation: Implications on Cellular Uptake and Drug Delivery *ACS Biomaterials Science & Engineering* 2016 2, 2153-2161.
Inward-Rectifier Potassium Channels and Effects on Membrane Potential
Bhave G, Lonergan D, Chauder B A, Denton J S. Small-molecule modulators of inward rectifier K+ channels: recent advances and future possibilities *Future Med Chem.* 2010 2: 757-774.

Wang H, Baofeng Yang B, Limin Zhang, Xu L, Wang, Z. Direct Block of Inward Rectifier Potassium Channels by Nicotine *Toxicology and Applied Pharmacology* 2000 164: 97-101.

Chen R, Swale D R. Inwardly Rectifying Potassium (Kir) Channels Represent a Critical Ion Conductance Pathway in the Nervous Systems of Insects *Scientific Reports* 2018 8:1617.

What is claimed is:

1. A construct comprising:
a gold nanoparticle conjugated to
a peptide comprising SEQ ID NO: 1 and a spacer sequence.

* * * * *

```
                        SEQUENCE LISTING

<160> NUMBER OF SEQ ID NOS: 3

<210> SEQ ID NO 1
<211> LENGTH: 21
<212> TYPE: PRT
<213> ORGANISM: Artificial Sequence
<220> FEATURE:
<223> OTHER INFORMATION: synthetic construct

<400> SEQUENCE: 1

Ala Leu Cys Asn Cys Asn Arg Ile Ile Ile Pro His Gln Cys Trp Lys
1               5                   10                  15

Lys Cys Gly Lys Lys
            20

<210> SEQ ID NO 2
<211> LENGTH: 6
<212> TYPE: PRT
<213> ORGANISM: Artificial Sequence
<220> FEATURE:
<223> OTHER INFORMATION: synthetic construct

<400> SEQUENCE: 2

Leu Ala Gly Trp Gly Pro
1               5

<210> SEQ ID NO 3
<211> LENGTH: 27
<212> TYPE: PRT
<213> ORGANISM: Artificial Sequence
<220> FEATURE:
<223> OTHER INFORMATION: synthetic construct

<400> SEQUENCE: 3

Leu Ala Gly Trp Gly Pro Ala Leu Cys Asn Cys Asn Arg Ile Ile Ile
1               5                   10                  15

Pro His Gln Cys Trp Lys Lys Cys Gly Lys Lys
            20                  25
```